(12) United States Patent
Cubb et al.

(10) Patent No.: US 7,182,728 B2
(45) Date of Patent: Feb. 27, 2007

(54) LARYNGOSCOPE WITH MULTI-DIRECTIONAL EYEPIECE

(75) Inventors: Anthony Cubb, Kingwood, TX (US); Natalie A. McCray, Celoron, NY (US)

(73) Assignee: Intubation Plus, Inc., Corry, PA (US)

( * ) Notice: Subject to any disclaimer, the term of this patent is extended or adjusted under 35 U.S.C. 154(b) by 551 days.

(21) Appl. No.: 10/201,738

(22) Filed: Jul. 24, 2002

(65) Prior Publication Data

US 2004/0019256 A1   Jan. 29, 2004

(51) Int. Cl.
*A61B 1/267* (2006.01)
(52) U.S. Cl. .................. 600/194; 600/187; 600/120; 600/199; 600/188
(58) Field of Classification Search ............... 600/120, 600/194, 185, 187, 188, 199
See application file for complete search history.

(56) References Cited

U.S. PATENT DOCUMENTS

| 4,267,828 A | 5/1981 | Matsuo |
| 4,437,458 A | 3/1984 | Upsher |
| 4,702,571 A | 10/1987 | Barber |
| 4,773,394 A | 9/1988 | Reichstein et al. |
| 4,834,518 A | 5/1989 | Barber |
| 4,838,245 A | 6/1989 | Storz |
| 4,885,667 A | 12/1989 | Selden |
| 5,287,848 A | 2/1994 | Cubb et al. |
| 5,377,668 A | 1/1995 | Ehmsen et al. |
| 5,632,553 A | 5/1997 | Huang |
| 5,643,221 A | 7/1997 | Bullard |
| 5,665,052 A | 9/1997 | Bullard |
| 5,941,818 A | 8/1999 | Hori et al. |
| 6,248,061 B1 | 6/2001 | Cook, Jr. |

OTHER PUBLICATIONS

New Zealand Examination Report dated Mar. 18, 2005.

*Primary Examiner*—John P. Leubecker
(74) *Attorney, Agent, or Firm*—Katten Muchin Rosenman LLP (57) ABSTRACT

A two piece endotracheal intubation device is provided having a multidirectional eyepiece, a suction port and a fiber optic assembly that enables a practitioner to apply suction to a patient's airway while at the same time visualizing the airway from any position relative to the patient for insertion of the endotracheal tube.

31 Claims, 7 Drawing Sheets

LARYNGOSCOPE WITH MULTI-DIRECTIONAL EYEPIECE

FIELD OF THE INVENTION

The present invention generally relates to an instrument for accessing the laryngeal area of a human body and, more particularly, to an improved laryngoscope for use in intubation.

BACKGROUND OF THE INVENTION

Laryngoscopes are widely known and used in the medical field to facilitate endotracheal intubation of a patient during an emergency situation to provide a positive air passageway for the mechanical ventilation of the lungs of the injured person. Such laryngoscopes are also used during surgical procedures to provide a passageway for the administration of anesthesia. In the human anatomy, the epiglottis normally overlies the glottis opening into the larynx to prevent the passage of food into the trachea during eating. Thus, when undertaking an endotracheal intubation, it is necessary to displace the epiglottis from the glottal opening to permit the air tube to be inserted into the trachea.

Various laryngoscope constructions are known. The more widely used laryngoscopes consist of an elongate, rigid metal blade which is supportably attached to a handle. These types of laryngoscopes are inserted through the mouth of the patient into the pharyngeal area to displace the tongue and epiglottis and permit direct visualization of the glottis through the mouth opening. Such laryngoscopes are generally provided with a light source which is directed along the blade to illuminate the area beyond the distal end of the blade.

The standard method for performing intubation of the trachea with conventional laryngoscope blades of the straight or slightly curved type is to place the patient in supine position, tilt the head backwards as far as possible, and distend the lower jaw to widely open the mouth. The blade is then inserted through the mouth into the throat passageway to displace the tongue and epiglottis and expose the glottis of the patient. The larynx is then viewed through the mouth opening from an observation position just above and behind the head of the patient by sighting generally along the axis of the blade. The endotracheal tube is inserted, either orally or transnasally, and passed alongside the blade through the glottis. The foregoing procedure is often made more difficult by the presence of bodily fluids on or in the larynx and trachea which significantly reduce the visibility when using conventional systems.

The safety and efficacy of procedures for introducing tubular members in the body can be greatly enhanced with the use of remote visualization, where for example, a distal end of an endoscope is introduced in the body to permit visualization of the procedures via an eyepiece of the endoscope optically coupled with an image receiving distal end. Introduction of tubular members with the assistance of remote visualization is highly desirable for various medical procedures; however, even with the assistance of remote visualization, many medical procedures involving introduction of tubular members remain difficult to perform and carry a risk of adverse consequences for the patient. In particular, it is difficult when introducing tubular members into the body to obtain accurate, clear exposure of sites in the body, such as the trachea, through which the tubular members are introduced. Without proper positioning and guidance, the tubular members often cause trauma or injury to anatomical tissue.

Surgical instruments having means for indirect illumination and visualization of the pharyngeal areas of the body are also known. U.S. Pat. Nos. 3,776,222 and 3,913,568 disclose devices for endotracheal intubation which comprise flexible or articulatable tubular probes having internal fiber optics for lighting and viewing the internal areas of the body. As disclosed in those patents, the probes carry a slidably removable endotracheal tube surrounding their outer surfaces and the probe is directly inserted into the trachea to position the tube. Such devices obviously require the use of relatively large diameter endotracheal tubes in order to be carried on the tubular probe, and their use necessarily is limited to patients with sufficiently large airway passages to accommodate the combined size of the probe and endotracheal tube. Additionally, due to the flexible nature of the probes, it is difficult to manipulate the probe to displace the tongue and epiglottis to permit direct insertion of the tube into the trachea.

As a consequence, there has been a long felt need for a device which can facilitate intubation so as to easily and quickly accomplish direct laryngoscopic intubation. There is a further need for such a device which is inexpensive enough to be financially accessible for any emergency vehicle. There is further also a need for such a device which enables indirect visualization of a patient's airway from a 360 degree vantage point.

SUMMARY OF THE INVENTION

The present invention is designed to overcome the aforementioned difficulties during intubation by providing a two piece endotracheal intubation device containing a light source, simultaneous suctioning ability, and a multidirectional eyepiece that enables a practitioner to apply suction to a patient's airway while at the same time visualizing the airway from any position relative to the patient for insertion of the endotracheal tube.

In one preferred embodiment, an endotracheal intubation is provided including an optical assembly enclosed by a housing where the optical assembly includes at least one optical fiber having a flexible distal portion and extending outwardly from a first end of the housing. A gooseneck fiber conduit is also provided that extends from a second end of the housing. The gooseneck is flexible along its length so as to be bent into a plurality of angular orientations with respect to the housing. An eyepiece is positioned at an end of the gooseneck having a lens system so that the at least one optical fiber optically communicates with the lens system through the gooseneck. A scabbard is provided for the optical assembly that is sized to receive a portion of the first end of the housing. The scabbard includes at least one optical fiber, and comprises a curved blade having a terminal edge surface and a plurality of spaced conduits longitudinally extending through the scabbard. Advantageously, a first one of the conduits extends longitudinally through the scabbard and opens onto the terminal edge surface of the scabbard. A second one of the conduits extends along an outer surface portion of the scabbard and defines an open channel that is sized to removably receive an endotracheal tube. A third one of the conduits extends longitudinally through the scabbard and comprises two open ends, one of which opens onto the terminal edge surface of the scabbard.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENT

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship. In the claims, means-plus-function clauses are intended to cover the structures described, suggested, or rendered obvious by the written description or drawings for performing the recited function, including not only structural equivalents but also equivalent structures.

The present invention provides a two piece endotracheal intubation device or intubator 5 that includes a multi-directional viewing assembly 8 which enables indirect visualization of a patient's airway from positions ranging 360 degrees around the patient. Two piece intubator 5 includes a fiber-scabbard 10 and an optical assembly 13. Fiber-scabbard 10 is formed from a hard polymer material formed so as to generally comprise the curved shape of a conventional intubation blade, e.g., a Macintosh or Miller blade. Fiber-scabbard 10 includes a proximal end 12 and a curved distal end 14. Proximal end 12 defines an open ended shroud 17 that is sized and shaped to accept a distal portion of optical assembly 13. An optical passageway 20 extends throughout the length of fiber-scabbard 10, and opens at the terminal face 21 of curved distal end 14. A proximal open end of an optical passageway 20 is located on the interior of shroud 17. A second passageway 27 also extends throughout the length of fiber-scabbard 10 in substantially parallel relation to optical passageway 20, and also opens at terminal face 21 of curved distal end 14. A port 24 is arranged below shroud 17, in fluid flow communication with second passageway 27. Direct suction may be applied to port 24 so that foreign material and secretions from the throat may be transferred through second passageway 27 thereby eliminating the need for suction catheters or the like. A channel formed on the outer curved surface of distal end 14 of fiber-scabbard 10 provides an endotracheal tube receptacle 30. Tube receptacle 30 is sized so as to snugly, but releasably accommodate an endotracheal tube 31 of the type well known in the art. Such a tube 31 may be prepositioned within tube receptacle 30 for direct intubation. A top opening 34 is partially obstructed by a plurality of spaced-apart, interdigitated fingers 36, which aid in snugly but releasably maintaining tube 31 within tube receptacle 30 during insertion of fiber-scabbard 10 into a patient's mouth and throat.

Figure 2:
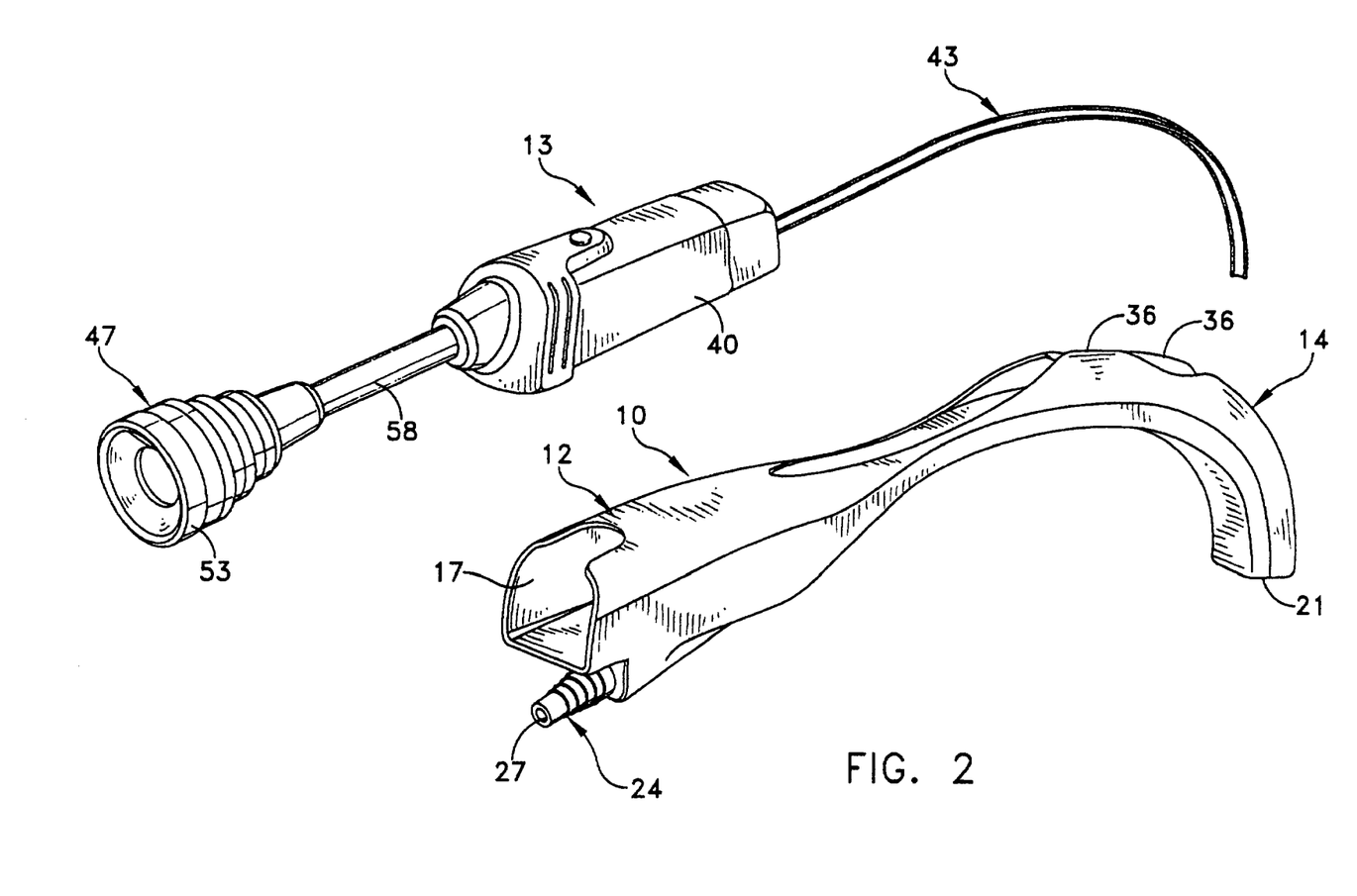
FIG. 2 is a perspective view of the two piece endotracheal intubation device shown FIG. 1, separated so as reveal a fiber optic system.
Figure 3:
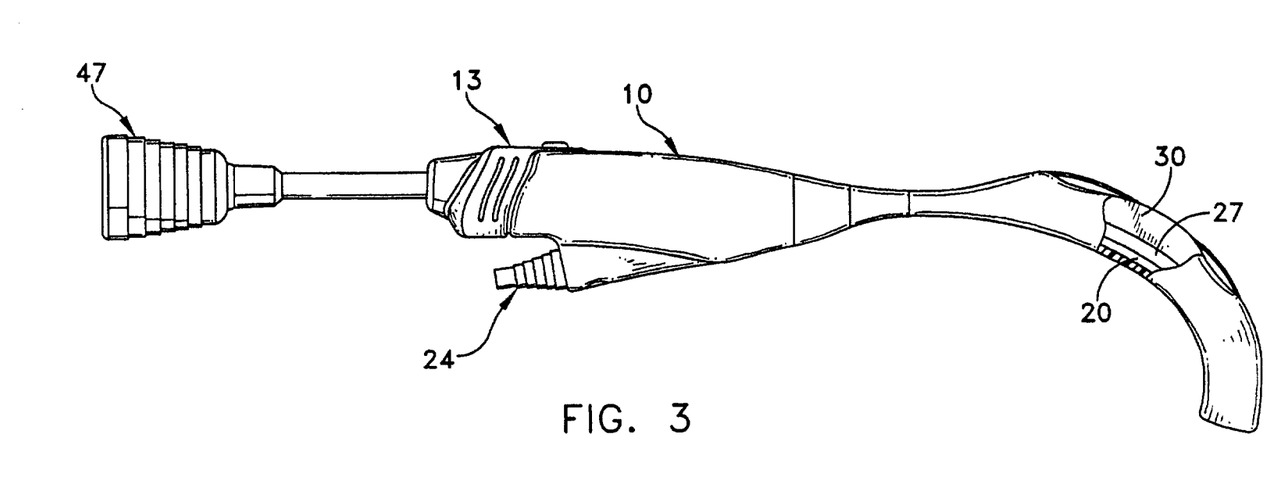
FIG. 3 is a side elevational view of the two piece endotracheal intubation device shown in FIG. 1.
Figure 4:
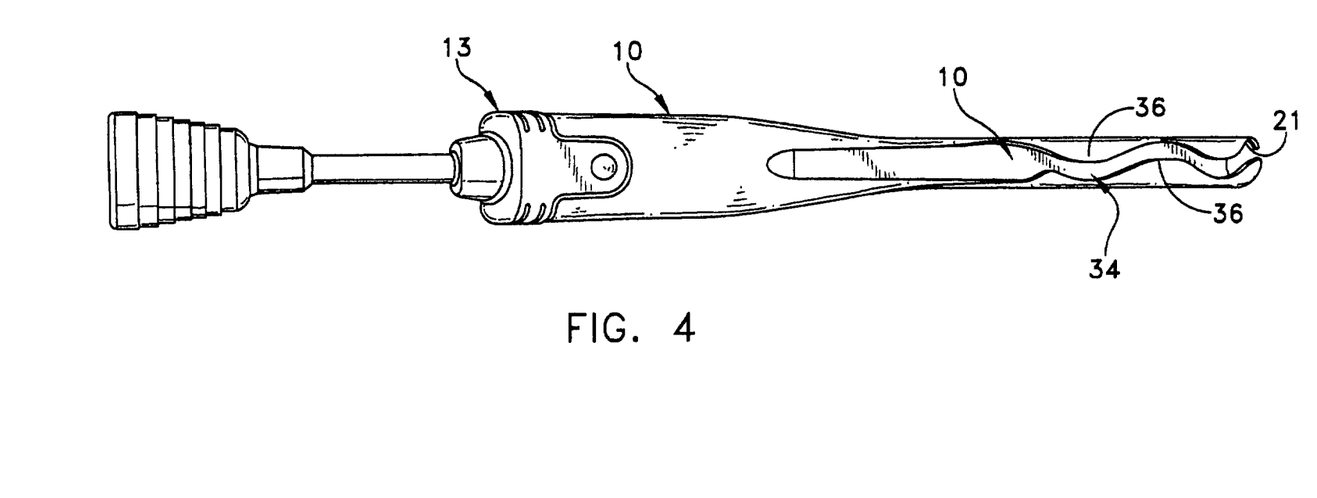
FIG. 4 is a top view of the two piece endotracheal intubation device shown in FIG. 3.
Figure 5:
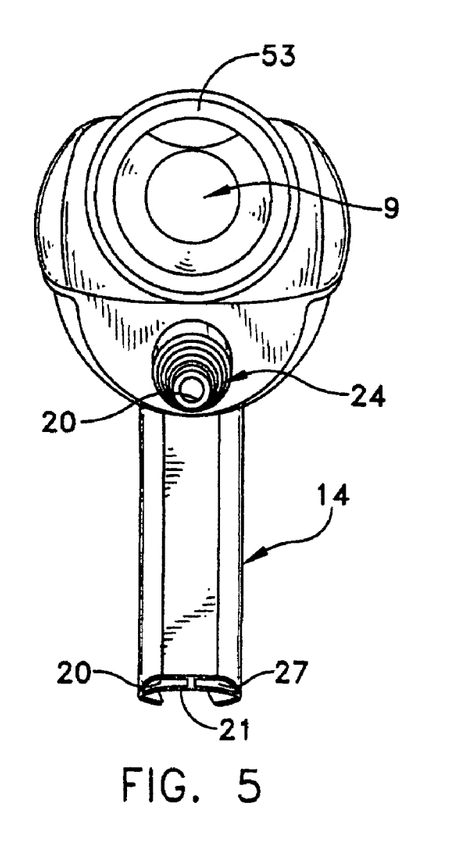
FIG. 5 is a rear-end view of the two piece endotracheal intubation device shown in FIG. 1.
Figure 6:
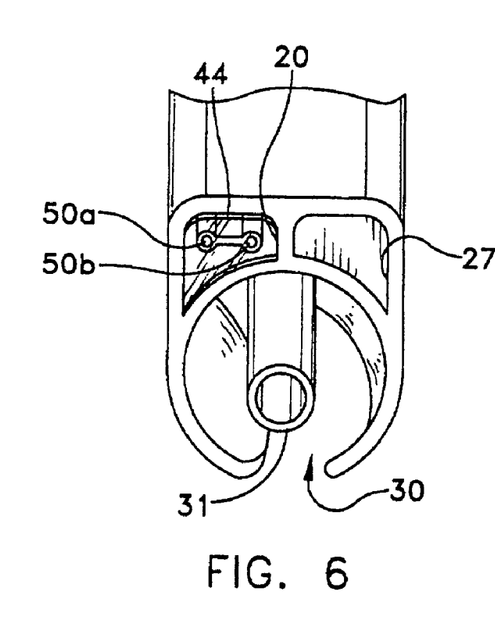
FIG. 6 is an end view of the fiber-scabbard having a endotracheal tube and fiber wand positioned with their respective conduits.

Optical assembly 13 includes a body housing 40, a fiber probe 43, and an adjustable eyepiece 47 (FIG. 2). Body housing 40 is sized and shaped to be releasably received within shroud 17 of fiber-scabbard 10. Body housing 40 encloses a conventional light source and associated battery power supply (not shown) with an on/off button 48 arranged so as to be easily accessible to an operator. Fiber probe 43 comprises an elongate, flexible probe that includes at least two optical fibers 50a and 50b, e.g., elongate, flexible strands of optical quality glass or a relatively rigid, light-conductive polymeric material, such as, methyl methacrylate. Optical fiber 50a is interconnected at one end to the light source within body housing 40, while the other end is open at the distal end of fiber probe 43. A lens 44 or similar light conditioning or focusing device may be sealingly disposed over the open end of optical passageway 20 at terminal face 21 of curved distal end 14 of fiber-scabbard 10, or over the free end of optical fiber 50a. This arrangement has the added benefit of preventing bodily fluids and the like from entering optical passageway 20 and contaminating fiber probe 43. Optical fiber 50b extends from the distal end of fiber probe 43, through body housing 40, and is optically interconnected with adjustable eyepiece 47. Adjustable eyepiece 47 comprises an ocular housing 53 disposed at one end of a "gooseneck" tube 58, and provides for ease of visualization of the larynx and trachea.

Figure 7:
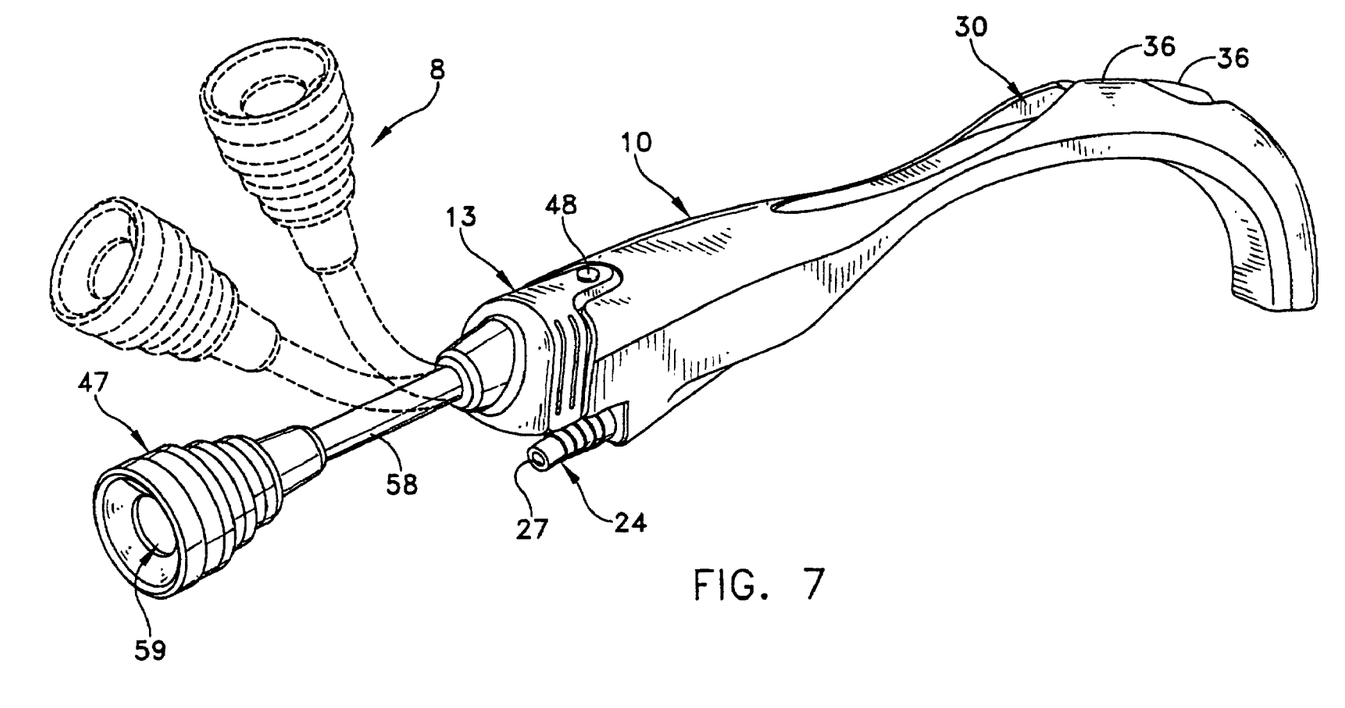
FIG. 7 is a perspective view, similar to FIG. 1, showing phantom positions into which the multi-directional viewing assembly of the two piece endotracheal intubation device may be swiveled.
Figure 8:
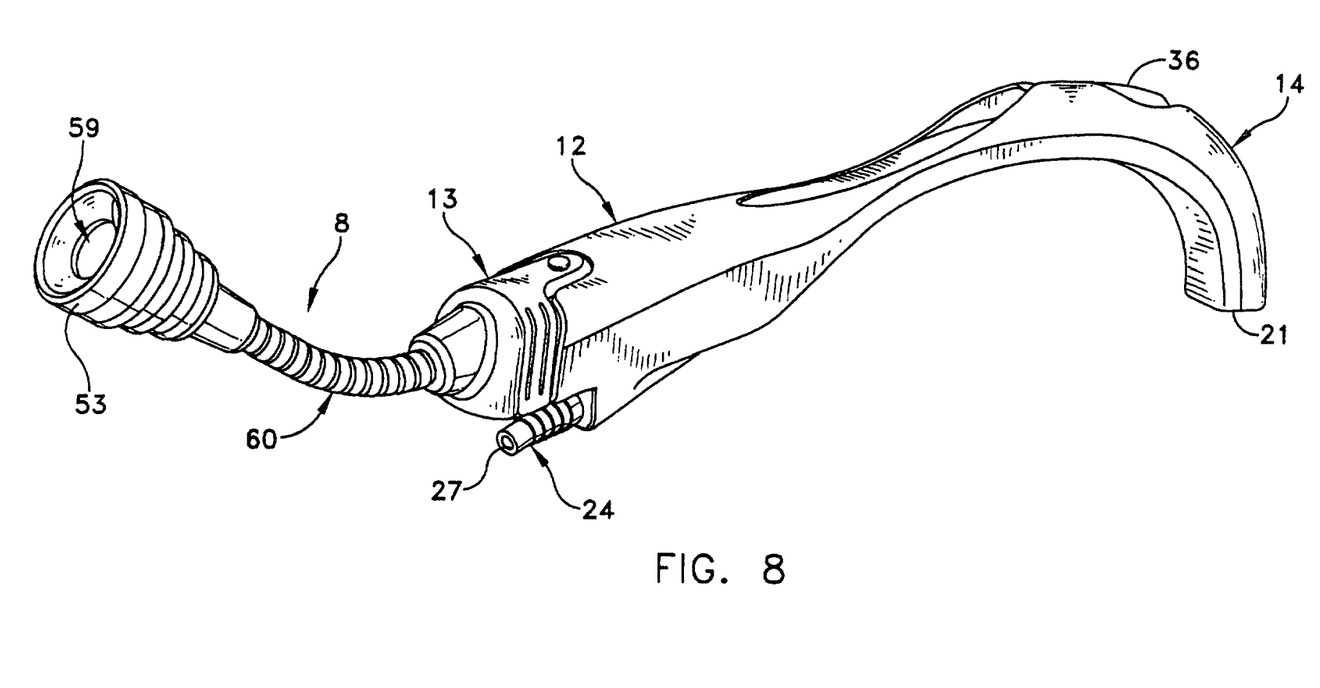
FIG. 8 is a perspective view, similar to FIG. 1, showing one embodiment of gooseneck tube.
Figure 9:
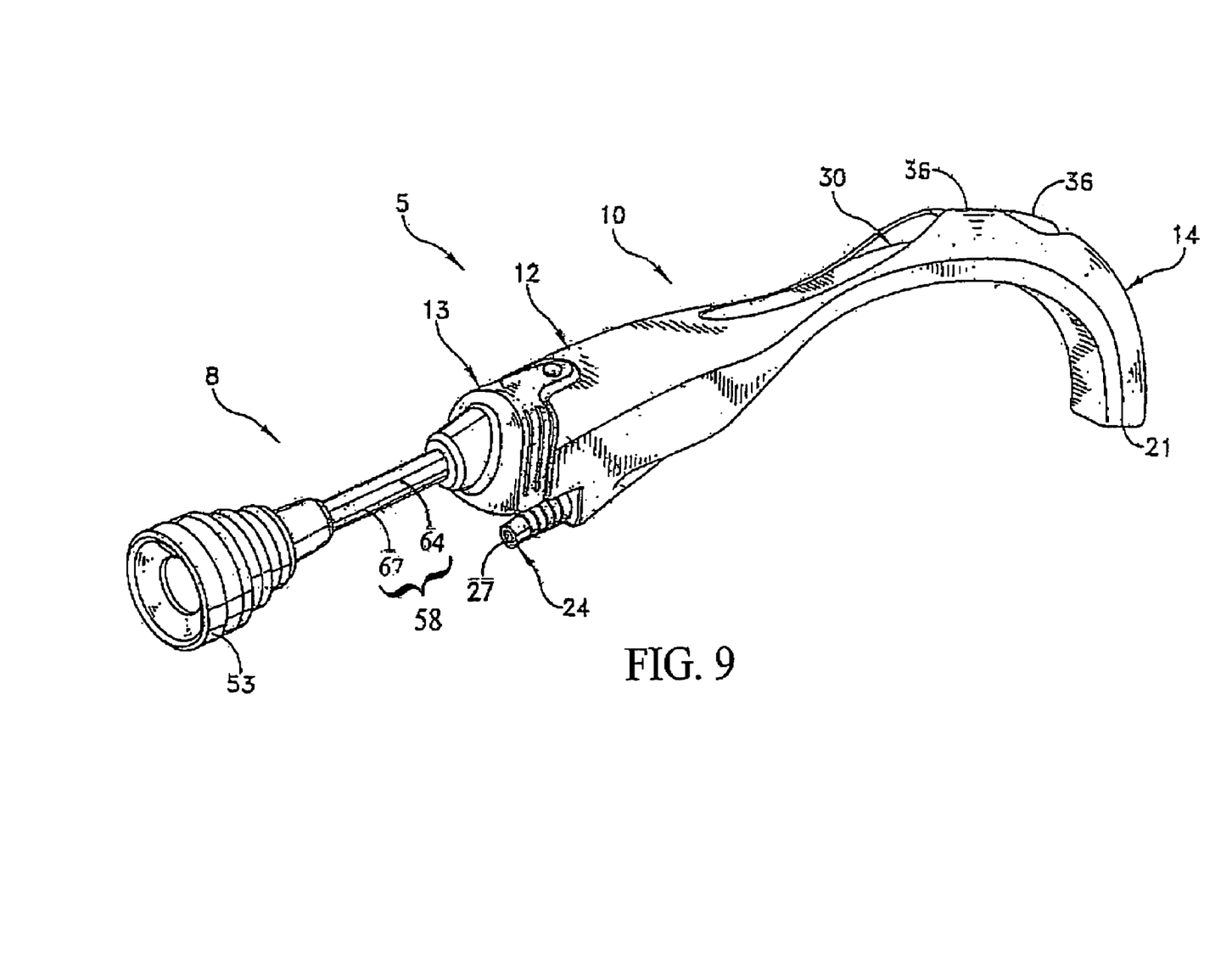
FIG. 9 is a perspective view, similar to FIG. 1, showing another embodiment of gooseneck tube.

Ocular housing 53 supports a conventional lens system 59 and is sized and shaped to allow a person to place their eye in close, focusing proximity to a conventional lens system 59 operatively mounted within ocular housing 53. Optical fiber 50b extends from body housing 40 to ocular housing 53 through gooseneck tube 58, and optically communicates with lens system 59. Gooseneck tube 58 may be formed of a coiled, interlocking metal strip 60 in a conventional manner, the interlocking being produced with a sufficiently frictional fit for supporting and maintaining ocular housing 53 in a desired position and orientation (FIGS. 7 and 8). For example, gooseneck 58 may be curved in a single plane or in orthogonal planes so as to allow for indirect visualization of a patient's airway from positions ranging 360 degrees around the patient's head. Alternatively, a bendable wire 64 may be placed within a flexible, resilient tube 67 so as to form gooseneck tube 58 (FIG. 9). In this alternative, bendable wire 64 extends the full length of gooseneck tube 58 or at least a substantial portion of its length. Bendable wire 64 is formed of a bendable or ductile metal so that it may take a set at a desired curvature and will tend to hold eyepiece 47 at that curvature in the absence of externally-applied reforming forces.

Figure 1:
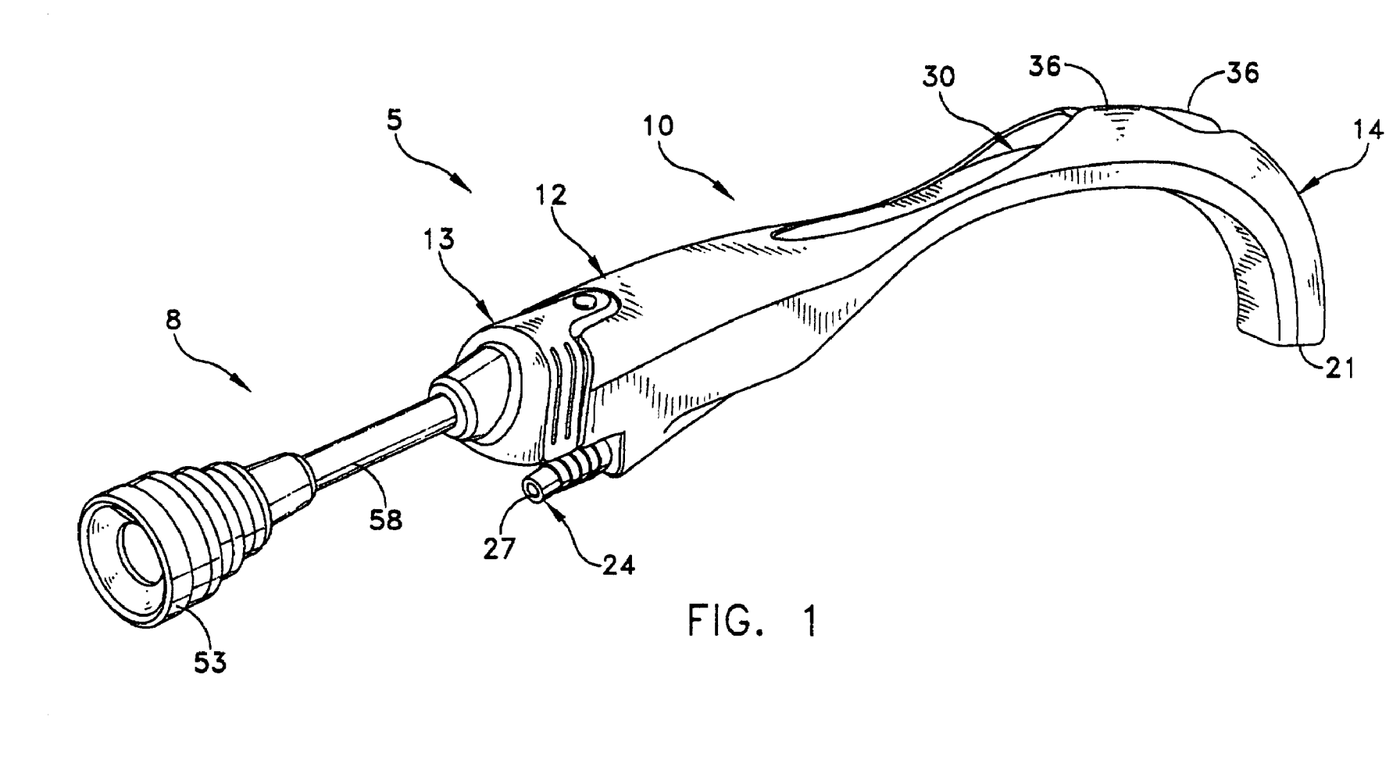
FIG. 1 is a perspective view of a two piece endotracheal intubation device having a multi-directional viewing assembly formed in accordance with the present invention.

Optical assembly 13 is positioned within fiber-scabbard 10 by inserting fiber probe 43 into the open proximal end of optical passageway 20. Once in this position, optical assembly 13 is moved toward the interior of shroud 17 until it enters fiber-scabbard 10 as shown in FIG. 1. In this position, the distal end of fiber probe 43 is positioned at terminal face 21 of curved distal end 14 of fiber-scabbard 10.

A tube 30 is then positioned within tube receptacle 30 of fiber-scabbard 10 by press-fitting it through the interdigitated fingers 36 so that it is held releasably in place within the outer portion of fiber-scabbard 10. Once this assembly is completed, an intubation procedure may be begun.

More particularly, and unlike conventional intubation devices, the patient's head need not be tilted backwards at all. Only the lower jaw needs to be somewhat distended, and the mouth open sufficiently to introduce two piece endotracheal intubation device 5. Curved distal end 14 of fiber-scabbard 10 is then inserted through the mouth into the throat passageway, so as to displace the tongue and epiglottis, and expose the glottis of the patient. Once in this position, suction may be applied to port 24, so as to draw bodily secretions and fluids away from the glottis and larynx through second passageway 27. Advantageously, this procedure may be visualized via viewing assembly 8 by swiveling or bending gooseneck tube 58, so as to position ocular housing 53 at a place convenient for the person performing the intubator to place their eye in close, focusing proximity to conventional lens system 59. It will be understood that viewing assembly 8 may be bent or maneuvered into a plurality of curved shapes, as needed, to provide for the comfort and access by the person forming the intubation and to allow for controlled viewing of the intubation process.

With the patient's larynx in view through eyepiece 47, tube 30 is maneuvered through the larynx and into the trachea of the patient, all the while being observed by the person performing the intubation. Once tube 30 has been properly positioned within the trachea, optical assembly 13 is first removed from fiber-scabbard 10 by simply pulling housing 40 out from within shroud 17, and moving optical assembly 13 away from proximal end 12 of fiber-scabbard 10 until fiber probe 43 has been removed from optical passage 20 and exited the open end of shroud 17. Once this procedure is completed, while holding tube 30, fiber-scabbard 10 is then slid along tube 30 until it exits the patient's mouth and can be removed from tube receptacle.

ADVANTAGES OF THE INVENTION

Numerous advantages are obtained by employing the present invention.

More specifically, an endotracheal intubation device is provided which avoids many of the aforementioned problems associated with prior art devices.

In addition, an endotracheal intubation device is provided which allows the operator to stand not only at the top of the patient's head while performing an intubation, (which is the only preferred) but also permits endotracheal tube placement under direct visualization of the target area, the larynx.

Furthermore, an endotracheal intubation device is provided in which an emergency care provider no longer needs to reposition or hyperextend the neck to facilitate visualization of the vocal cords, such as in the case of an automobile accident when the person in need of respiratory assistance and there is a potential threat of neck or cervical spine injuries, which can lead to further neck, spine, and spinal cord damage, and even paralysis.

Also, an endotracheal intubation device is provided which does not require the hyperextension of the neck to visualize the vocal cords and other anatomy, thus alleviating previous intubation problems, such as broken or chipped teeth.

In addition, an endotracheal intubation device is provided, including an eyepiece that may be oriented 360° about the patient's mouth and head, so as to allow the operator to intubate through a car window or in tight or closed spaces, something that a conventional emergency care-giver has not been able to do. This is extremely helpful when a victim is trapped inside of a car where they would normally not be able to be intubated.

Furthermore, an endotracheal intubation device is provided having a multi-directional viewing assembly that permits intubation from the side of a bed in a medical care facility. Previously, such intubation had to be performed from only the head of the bed, necessitating removal of the headboard of the bed to create a space between the bed and the wall, and the person maneuvering him/herself through the numerous intravenous lines and monitor equipment to be able to stand between the wall and the head of the bed, in order to place the endotracheal tube within the patient's trachea.

Also, an endotracheal intubation device is provided having the flexibility of a gooseneck assembly, so that the viewer is allowed to move an image in the eyepiece, clockwise or counterclockwise, nearly a full 360° about the patient's head, thereby allowing for a plurality of positions.

Also, an endotracheal intubation device is provided having front to back flexion of the viewing assembly in relationship to the body of the device allowing for near full flexion to allow the operator to be located anywhere, e.g., at the head of the victim, on the side of the victim, or along the body of the victim, etc., for better positioning during endotracheal intubation, with direct visualization of the vocal cords.

In addition, an endotracheal intubation device is provided, having the capability to be used to intubate from the side of a patient, thereby decreasing the spread of infectious diseases and other bacterial matter to the operator by not having to hyperextend the neck to see the vocal cords, and thereby decreasing the risk of coughing up into the operator's eyes and face, secretions laden with infectious diseases, such as HIV, hepatitis, multi-drug resistant TB, etc.

In addition, an endotracheal intubation device is provided, having a rotational eyepiece that permits intubation through a car window, or when an accident victim is trapped inside an automobile.

It is to be understood that the present invention is by no means limited only to the particular constructions herein disclosed and shown in the drawings, but also comprises any modifications or equivalents within the scope of the claims.

What is claimed is:

1. An endotracheal intubation device comprising:
   an optical assembly enclosed by a housing, said optical assembly including at least one optical fiber having a flexible distal portion and extending outwardly from a first end of said housing and a gooseneck fiber conduit extending from a second end of said housing, said gooseneck being flexible along its length so as to be bent into a plurality of angular orientations with respect to said housing, and including an eyepiece having a lens system and positioned at an end of said gooseneck wherein said at least one optical fiber optically communicates with said lens system through said gooseneck; and
   a scabbard sized to receive a portion of said first end of said housing including the at least one optical fiber, wherein said scabbard comprises a curved blade having a terminal edge surface and a plurality of spaced conduits wherein: (i) a first one of said conduits extends longitudinally through said scabbard and has at least one optically open end at said terminal edge surface of said scabbard, said optically open end being fluid impervious, (ii) a second one of said conduits extends along an outer surface portion of said scabbard and defines an open channel that is sized to removably receive an endotracheal tube, and (iii) a third one of said conduits extends longitudinally through said scabbard and comprises two open ends, one of which opens onto said terminal edge surface of said scabbard; wherein the housing further contains a light source and a power source for the light source.

2. An endotracheal intubation device according to claim 1 wherein said scabbard is formed from a polymer so as to comprise a curved intubation blade.

3. An endotracheal intubation device according to claim 1 wherein said scabbard includes a proximal end that defines an open ended shroud that is sized and shaped to accept a distal portion of said housing.

4. An endotracheal intubation device according to claim 3 comprising a port arranged below said shroud, in fluid flow communication with said second open end of said third conduit.

5. An endotracheal intubation device according to claim 1 wherein said open channel provides a receptacle that is sized so as to snugly, but releasably accommodate said endotracheal tube.

6. An endotracheal intubation device according to claim 1 wherein said open channel is partially obstructed by a plurality of spaced-apart, interdigitated fingers.

7. An endotracheal intubation device according to claim 1 wherein a distal portion of said housing is sized and shaped to be releasably received within a proximal end of said scabbard that defines an open ended shroud and within which is defined an open end of said first one of said conduits.

8. An endotracheal intubation device according to claim 1 wherein said at least one optical fiber is elongate and flexible.

9. An endotracheal intubation device according to claim 1 having a lens sealingly disposed over said open end of said first one of said conduits on said terminal edge surface.

10. An endotracheal intubation device according to claim 1 wherein said gooseneck fiber conduit comprises a tube formed on a coiled, interlocking metal strip where the interlocking is produced with a sufficiently frictional fit for supporting and maintaining said gooseneck in a desired position and orientation.

11. An endotracheal intubation device according to claim 10 wherein said gooseneck may be curved in a single plane or in orthogonal planes so as to allow for positions ranging 360 degrees around said second end of said housing.

12. An endotracheal intubation device according to claim 1 wherein said gooseneck fiber conduit comprises a bendable wire placed within a flexible, resilient tube and extends the fall length of said gooseneck where said wire is formed of a bendable or ductile metal so that it may take a set at a desired curvature and will tend to said curvature in the absence of externally-applied re-forming forces.

13. An endotracheal intubation device comprising:
   an optical assembly enclosed by a housing;
   a scabbard portion sized to receive a portion of said optical assembly, wherein said scabbard portion comprises a blade having a terminal edge;
   a plurality of spaced conduits;
   one of said conduits extending along an outer surface portion of said scabbard portion, having an open edge, and being sized to removably receive an endotracheal tube;
   a second of said conduits longitudinally extending through said scabbard and penetrating said terminal edge of said scabbard portion; and
   a third of said conduits longitudinally extending through said scabbard and penetrating said terminal edge of said scabbard portion and sized to receive an optical fiber to (i) communicate with a light source for illuminating the area into which the endotracheal tube is to be positioned, and (ii) to receive images from the illuminated area, said third conduit being fluid impervious at the terminal end of the scabbard portion; wherein said
   optical fiber has a flexible distal portion insertable into said third of said conduits and a proximal end extending into and optically communicating with said optical assembly enclosed by said housing, said optical assembly further comprising a gooseneck that is flexible along its length such that it may be bent into a plurality of angular orientations with respect to said housing and an eyepiece positioned at an end of said gooseneck; wherein the housing further contains the light source and a power source for the light source.

14. An endotracheal intubation device according to claim 13 wherein said scabbard portion is formed from a polymer so as to comprise a carved intubation blade.

15. An endotracheal intubation device according to claim 13 wherein said scabbard portion includes a proximal end that defines an open ended shroud that is sized and shaped to accept a distal portion of said housing.

16. An endotracheal intubation device according to claim 15 comprising a port arranged below said shroud, in fluid flow communication with said second conduit.

17. An endotracheal intubation device according to claim 13 wherein said open edge of said one of said conduits defines the mouth of a channel so as to provide a receptacle that is sized so as to snugly, but releasably accommodate said endotracheal tube.

18. An endotracheal intubation device according to claim 17 wherein said channel is partially obstructed by a plurality of spaced-apart, interdigitated fingers.

19. An endotracheal intubation device according to claim 13 wherein a distal portion of said housing is sized and shaped to be releasably received within a proximal end of said scabbard portion that defines an open ended shroud.

20. An endotracheal intubation device according to claim 13 wherein said optical fiber is an elongate and flexible bundle of at least two optical fibers.

21. An endotracheal intubation device according to claim 13 having a lens sealingly disposed over a open end of said third conduit on said terminal edge.

22. An endotracheal intubation device according to claim 13 wherein said gooseneck comprises a tube formed of a coiled, interlocking metal ship where the interlocking is produced with a sufficiently frictional fit for supporting and maintaining said gooseneck in a desired position and orientation.

23. An endotracheal intubation device according to claim 13 wherein said gooseneck may be curved in a single plane or in orthogonal planes so as to allow for positions ranging 360 degrees around said second end of said housing.

24. An endotracheal intubation device according to claim 13 wherein said gooseneck comprises a bendable wire placed within a flexible, resilient tube and extends the full length of said gooseneck where said wire is formed of a bendable or ductile metal so that it may take a set at a desire curvature and will tend to said curvature in the absence of externally-applied re-forming forces.

25. An endotracheal intubation device comprising:
an optical assembly enclosed by a housing, said optical assembly including at least one optical fiber having a flexible distal portion and extending outwardly from a first end of said housing and a gooseneck fiber conduit extending from a second end of said housing, said gooseneck being flexible along its length so as to be bent into a plurality of angular orientations with respect to said housing, and including an eyepiece having a lens system and positioned at an end of said gooseneck wherein said at least one optical fiber optically communicates with said lens system through said gooseneck, said housing further enclosing a light source and a power source for the light source; and
a scabbard sized to receive a portion of said first end of said housing including at least one optical fiber, wherein said scabbard comprises a curved blade having a terminal edge surface and a plurality of spaced conduits wherein: (i) a first one of said conduits extends longitudinally through said scabbard and has at least one optically open end at said terminal edge surface of said scabbard, said optically open end being fluid impervious (ii) a second one of said conduits extends along an outer surface portion of said scabbard and defines an open channel that is sized to removably receive an endotracheal tube, wherein said open channel includes a plurality of interdigitated fingers, and (iii) a third one of said conduits extends longitudinally through said scabbard and comprises two open ends, one of which opens onto said terminal edge surface of said scabbard.

26. An endotracheal intubation device comprising:
an optical assembly enclosed by a housing, said optical assembly including at least one optical fiber having a flexible distal portion and extending outwardly from a first end of said housing and a gooseneck fiber conduit extending from a second end of said housing, said gooseneck being flexible along its length so as to be bent into a plurality of angular orientations with respect to said housing, and including an eyepiece having a lens system and positioned at an end of said gooseneck wherein said at least one optical fiber optically communicates with said lens system through said gooseneck, said housing further enclosing a light source and a power source for the light source; and
a scabbard sized to receive a portion of said first end of said housing and including at least one optical fiber, wherein said scabbard comprises a curved blade having a terminal edge surface and a plurality of spaced conduits wherein: (i) a first one of said conduits extends longitudinally through said scabbard and has at least one optically open end at said terminal edge surface of said scabbard, said optically open end being fluid impervious (ii) a second one of said conduits extends along an outer surface portion of said scabbard and defines an open channel that is sized to removably receive an endotracheal tube, and (iii) a third one of said conduits extends longitudinally trough said scabbard and comprises two open ends, one of which opens onto said terminal edge surface of said scabbard;
wherein said gooseneck fiber conduit comprises a tube formed of a coiled, interlocking metal strip where the interlocking is produced with a sufficiently frictional fit for supporting and maintaining said gooseneck in a desired position and orientation.

27. Au endotracheal intubation device comprising:
an optical assembly enclosed by a housing, said optical assembly including at least one optical fiber having a flexible distal portion and extending outwardly from a first end of said housing and a gooseneck fiber conduit extending from a second end of said housing, said gooseneck being flexible along its length so as to be bent into a plurality of angular orientations with respect to said housing, and including an eyepiece having a lens system and positioned at an end of said gooseneck wherein said at least one optical fiber optically communicates with said lens system through said gooseneck, said housing further enclosing a light source and a power source for the light source; and
a scabbard sized to receive a portion of said first end of said housing and including at least one optical fiber, wherein said scabbard comprises a curved blade having a terminal edge surface and a plurality of spaced conduits wherein: (i) a first one of said conduits extends longitudinally through said scabbard and has at least one optically open end at said terminal edge surface of said scabbard, said optically open end being fluid impervious (ii) a second one of said conduits extends along an outer surface portion of said scabbard and defines an open channel that is sized to removably receive an endotracheal tube, and (iii) a third one of said conduits extends longitudinally through said scabbard and comprises two open ends, one of which opens onto said terminal edge surface of said scabbard;
wherein said gooseneck fiber conduit comprises a bendable wire placed within a flexible, resilient tube and extends the full length of said gooseneck where said wire is formed of a bendable or ductile metal so that it may take a set at a desired curvature and will tend to said curvature in the absence of externally-applied re-forming forces.

28. An endotracheal intubation device comprising:
an optical assembly enclosed by a housing, said housing further enclosing a light source and a power source for the light source;
a scabbard portion sized to receive a portion of said optical assembly, wherein said scabbard portion comprises a blade having a terminal edge;
a plurality of spaced conduits one of said conduits extending along an outer surface of said scabbard portion, having an open edge, and being sized to removably receive an endotracheal tube;

a second of said conduits longitudinally extending through said scabbard and penetrating said terminal edge of said scabbard portion; and a third of said conduits longitudinally extending through said scabbard and penetrating said terminal edge of said scabbard portion and sized to receive an optical fiber to (i) communicate with the light source for illuminating the area into which the endotracheal tube is to be positioned, and (ii) to receive images from the illuminated area, said third conduit being fluid impermeable at the terminal end of the scabbard portion; wherein said optical fiber has a flexible distal portion insertable into said third of said conduits and a proximal end extending into and optically communicating with said optical assembly enclosed by said housing, said optical assembly further comprising a gooseneck that is flexible along its length such that it may be bent into a plurality of angular orientations with respect to said housing and an eyepiece positioned at an end of said gooseneck;

wherein said open edge of said one of said conduits defines the mouth of a channel so as to provide a receptacle that is sized so as to snugly, but releasably accommodate said endotracheal tube.

29. An endotracheal intubation device comprising:

an optical assembly enclosed by a housing, said housing further enclosing a light source and a power source for the light source;

a scabbard portion sized to receive a portion of said optical assembly, wherein said scabbard portion comprises a blade having a terminal edge;

a plurality of spaced conduits;

one of said conduits extending the along an outer surface portion of said scabbard portion, having an open edge, and being sized to removably receive an endotracheal tube;

a second of said conduits longitudinally extending through said scabbard and penetrating said terminal edge of said scabbard portion; and a third of said conduits longitudinally extending through said scabbard and penetrating said terminal edge of said scabbard portion and sized to receive an optical fiber to (i) communicate with the light source for illuminating the area into which the endotracheal tube is to be positioned, and (ii) to receive images from the illuminated area, said third conduit being liquid impervious at the terminal end of the scabbard portion; wherein said optical fiber has a flexible distal portion insertable into said third of said conduits and a proximal end extending into and optically communicating with said optical assembly enclosed by said housing, said optical assembly further comprising a gooseneck that is flexible along its length such that it may be bent into a plurality of angular orientations with respect to said housing and an eyepiece positioned at an end of said gooseneck;

wherein said gooseneck comprises a tube formed of a coiled, interlocking metal strip where the interlocking is produced with a sufficiently frictional fit for supporting and maintaining said gooseneck in a desired position and orientation.

30. An endotracheal intubation device comprising:

an optical assembly enclosed by a housing, said housing further enclosing a light source and a power source for the light source;

a scabbard portion sized to receive a portion of said optical assembly, wherein said scabbard portion comprises a blade having a terminal edge;

a plurality of spaced conduits;

one of said conduits extending the along an outer surface portion of said scabbard portion, having an open edge, and being sized to removably receive an endotracheal tube;

a second of said conduits longitudinally extending through said scabbard and penetrating said terminal edge of said scabbard portion; and a third of said conduits longitudinally extending through said scabbard and penetrating said terminal edge of said scabbard portion and sized to receive an optical fiber to (i) communicate with the light source for illuminating the area into which the endotracheal tube is to be positioned, and (ii) to receive images from the illuminated area, said third conduit being fluid impervious at the terminal end of the scabbard portion; wherein said optical fiber has a flexible distal portion insertable into said third of said conduits and a proximal end extending into and optically communicating with said optical assembly enclosed by said housing, said optical assembly further comprising a gooseneck that is flexible along its length such that it may be bent into a plurality of angular orientations with respect to said housing and an eyepiece positioned at an end of said gooseneck;

wherein said gooseneck comprises a bendable wire placed within a flexible, resilient tube and extends full length of said gooseneck where said wire is formed of a bendable or ductile metal so that it may take a set at a desired curvature and will tend to said curvature in the absence of externally-applied re-forming forces.

31. An endotracheal intubation device comprising:

a housing enclosing an optical assembly including a light source and a power source, said housing having an optical fiber extending in a first direction therefrom, and a gooseneck fiber conduit extending in a second direction therefrom, and means for engaging said light source;

a scabbard for endotracheal insertion into a patient, the scabbard comprising a curved blade end and an open end for releasably receiving the housing, wherein said housing is received into the scabbard when the housing and scabbard are substantially in-line with one another such that said intubation device may be inserted into a patient from angle about the patients head.

* * * * *